United States Patent
Sullivan et al.

(10) Patent No.: US 10,086,209 B2
(45) Date of Patent: Oct. 2, 2018

(54) SELECTIVE POST-SHOCK TRANSTHORACIC PACING

(71) Applicant: Physio-Control, Inc., Redmond, WA (US)

(72) Inventors: Joseph L. Sullivan, Kirkland, WA (US); Fred Chapman, Newcastle, WA (US)

(73) Assignee: PHYSIO-CONTROL, INC., Redmond, WA (US)

( * ) Notice: Subject to any disclaimer, the term of this patent is extended or adjusted under 35 U.S.C. 154(b) by 472 days.

(21) Appl. No.: 14/292,720

(22) Filed: May 30, 2014

(65) Prior Publication Data

US 2014/0358048 A1 Dec. 4, 2014

Related U.S. Application Data

(60) Provisional application No. 61/829,014, filed on May 30, 2013.

(51) Int. Cl.
*A61N 1/00* (2006.01)
*A61N 1/39* (2006.01)
*A61N 1/365* (2006.01)
*A61H 31/00* (2006.01)

(52) U.S. Cl.
CPC ......... *A61N 1/3925* (2013.01); *A61H 31/005* (2013.01); *A61N 1/36514* (2013.01); *A61H 2201/5007* (2013.01); *A61H 2201/5043* (2013.01); *A61H 2201/5061* (2013.01); *A61H 2201/5097* (2013.01); *A61H 2230/045* (2013.01); *A61H 2230/208* (2013.01); *A61H 2230/255* (2013.01)

(58) Field of Classification Search
CPC ....................................................... A61N 1/046
USPC ............................................. 607/2, 5, 7, 142
See application file for complete search history.

(56) References Cited

U.S. PATENT DOCUMENTS

| | | |
|---|---|---|
| 5,391,187 A | 2/1995 | Freeman |
| 8,099,163 B2 | 1/2012 | Jung et al. |
| 8,219,192 B2 | 7/2012 | Shuros et al. |
| 8,725,253 B2 * | 5/2014 | Johnson et al. ................. 607/5 |
| 2004/0172066 A1 | 9/2004 | Wagner et al. |
| 2006/0122649 A1 | 6/2006 | Ghanem et al. |
| 2011/0202100 A1 * | 8/2011 | Tan et al. ........................ 607/6 |

* cited by examiner

*Primary Examiner* — Nadia A Mahmood
(74) *Attorney, Agent, or Firm* — Lane Powell PC

(57) ABSTRACT

A medical device can include a housing, an energy storage module within the housing to store an electrical charge, and a defibrillation port to guide via electrodes the stored electrical charge to a person in need of medical assistance. The medical device can also include a processor to perform a patient signal analysis on an electrocardiogram (ECG) signal corresponding to the person and further determine, based on a result of the patient signal analysis, whether post-shock transcutaneous pacing should be performed on the person.

23 Claims, 9 Drawing Sheets

*DEFIBRILLATION SCENE*

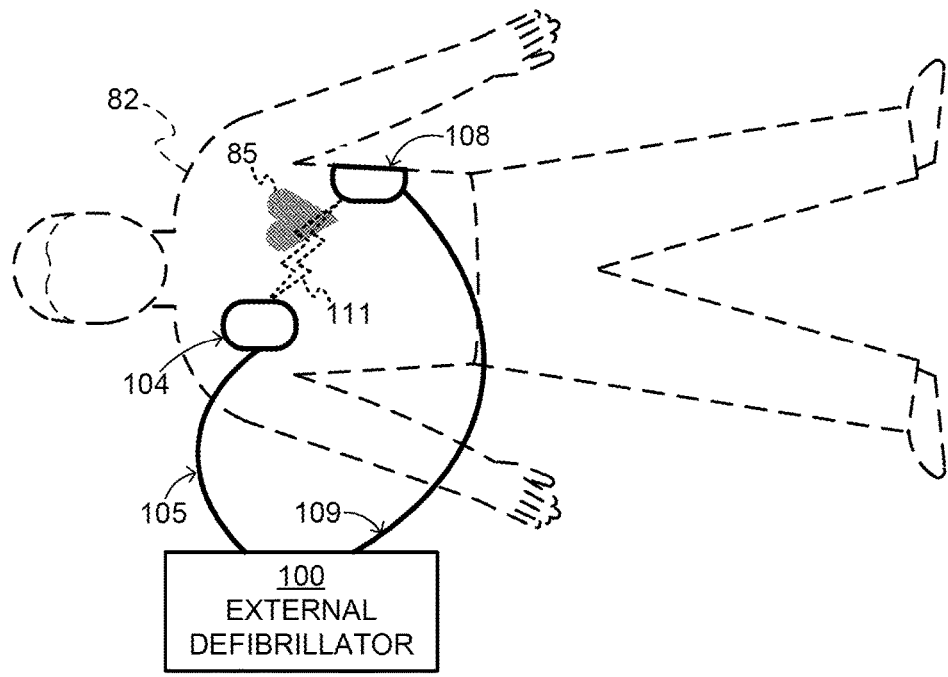
FIG. 1  *DEFIBRILLATION SCENE*
| TYPE OF EXTERNAL DEFIBRILLATOR | INTENDED TO BE USED BY PERSONS: | |
|---|---|---|
| | IN THE MEDICAL PROFESSIONS | NOT IN THE MEDICAL PROFESSIONS |
| DEFIBRILLATOR – MONITOR | √ | |
| AED | √ | √ |
FIG. 2  *TWO MAIN TYPES OF EXTERNAL DEFIBRILLATORS*

COMPONENTS OF EXTERNAL DEFIBRILLATOR

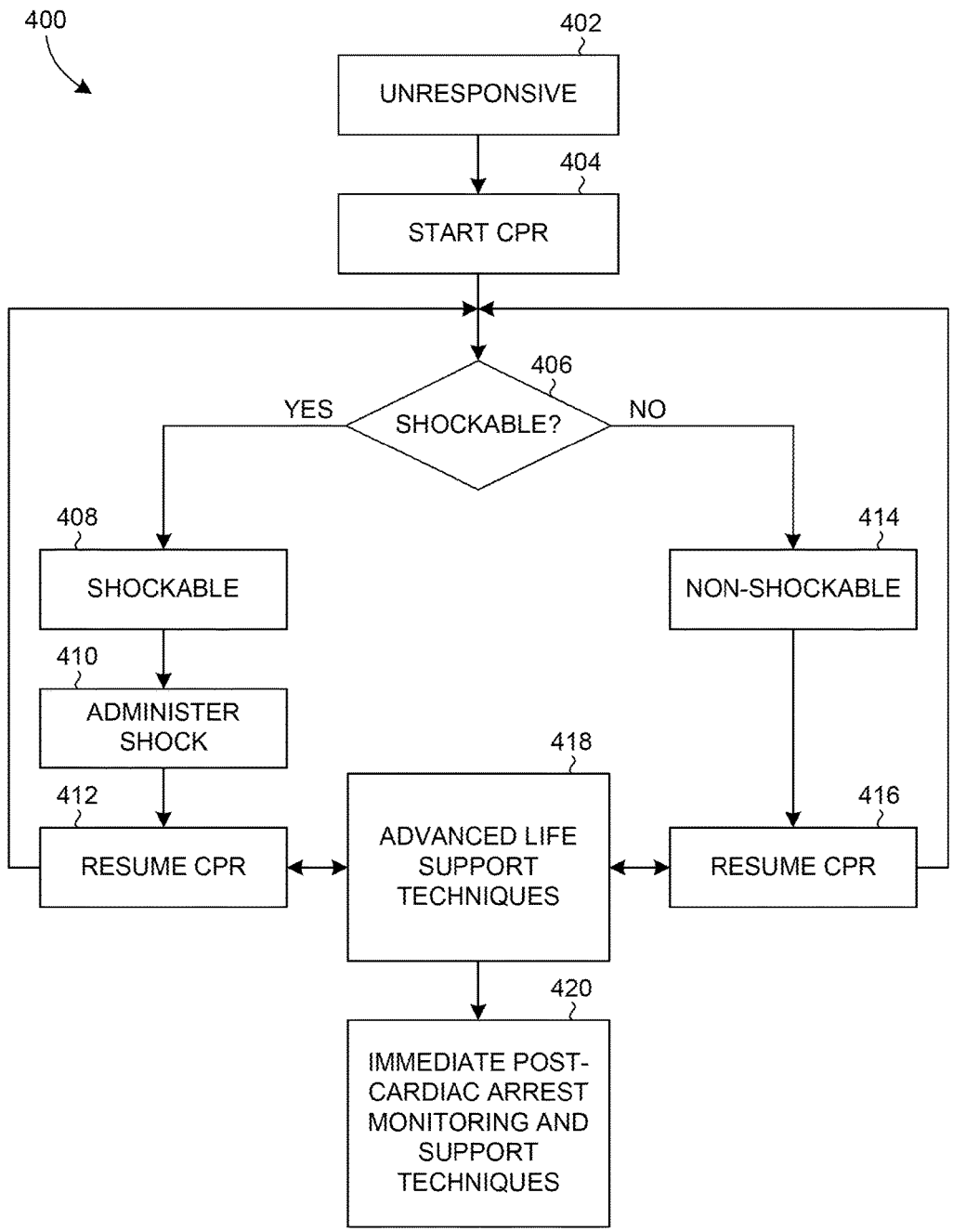
FIG. 4
(Conventional)

SELECTIVE POST-SHOCK TRANSTHORACIC PACING

PRIORITY CLAIM

This application claims the benefit of U.S. Provisional Patent Application Ser. No. 61/829,014, filed May 30, 2013 and titled SELECTIVE POST-SHOCK TRANSTHORACIC PACING, the content of which is hereby fully incorporated by reference herein.

FIELD

This invention generally relates to medical devices, such as external defibrillators.

BACKGROUND

In humans, the heart beats to sustain life. In normal operation, it pumps blood through the various parts of the body. More particularly, the various chamber of the heart contract and expand in a periodic and coordinated fashion, which causes the blood to be pumped regularly. More specifically, the right atrium sends deoxygenated blood into the right ventricle. The right ventricle pumps the blood to the lungs, where it becomes oxygenated, and from where it returns to the left atrium. The left atrium pumps the oxygenated blood to the left ventricle. The left ventricle, then, expels the blood, forcing it to circulate to the various parts of the body.

The heart chambers pump because of the heart's electrical control system. More particularly, the sinoatrial (SA) node generates an electrical impulse, which generates further electrical signals. These further signals cause the above-described contractions of the various chambers in the heart, in the correct sequence. The electrical pattern created by the sinoatrial (SA) node is called a sinus rhythm.

Sometimes, however, the electrical control system of the heart malfunctions, which can cause the heart to beat irregularly, or not at all. The cardiac rhythm is then generally called an arrhythmia. Arrhythmias may be caused by electrical activity from locations in the heart other than the SA node. Some types of arrhythmia may result in inadequate blood flow, thus reducing the amount of blood pumped to the various parts of the body. Some arrhythmias may even result in a Sudden Cardiac Arrest (SCA). In a SCA, the heart fails to pump blood effectively, and, if not treated, death can occur. In fact, it is estimated that SCA results in more than 250,000 deaths per year in the United States alone. Further, a SCA may result from a condition other than an arrhythmia.

One type of arrhythmia associated with SCA is known as Ventricular Fibrillation (VF). VF is a type of malfunction where the ventricles make rapid, uncoordinated movements, instead of the normal contractions. When that happens, the heart does not pump enough blood to deliver enough oxygen to the vital organs. The person's condition will deteriorate rapidly and, if not reversed in time, they will die soon, e.g. within ten minutes.

Ventricular Fibrillation can often be reversed using a life-saving device called a defibrillator. A defibrillator, if applied properly, can administer an electrical shock to the heart. The shock may terminate the VF, thus giving the heart the opportunity to resume pumping blood. If VF is not terminated, the shock may be repeated, often at escalating energies.

A challenge with defibrillation is that the electrical shock must be administered very soon after the onset of VF. There is not much time: the survival rate of persons suffering from VF decreases by about 10% for each minute the administration of a defibrillation shock is delayed. After about 10 minutes the rate of survival for SCA victims averages less than 2%.

The challenge of defibrillating early after the onset of VF is being met in a number of ways. First, for some people who are considered to be at a higher risk of VF or other heart arrhythmias, an Implantable Cardioverter Defibrillator (ICD) can be implanted surgically. An ICD can monitor the person's heart, and administer an electrical shock as needed. As such, an ICD reduces the need to have the higher-risk person be monitored constantly by medical personnel.

Regardless, VF can occur unpredictably, even to a person who is not considered at risk. As such, VF can be experienced by many people who lack the benefit of ICD therapy. When VF occurs to a person who does not have an ICD, they collapse, because blood flow has stopped. They should receive therapy quickly.

For a VF victim without an ICD, a different type of defibrillator can be used, which is called an external defibrillator. External defibrillators have been made portable, so they can be brought to a potential VF victim quickly enough to revive them.

During VF, the person's condition deteriorates, because the blood is not flowing to the brain, heart, lungs, and other organs. Blood flow must be restored, if resuscitation attempts are to be successful.

Cardiopulmonary Resuscitation (CPR) is one method of forcing blood flow in a person experiencing cardiac arrest. In addition, CPR is the primary recommended treatment for some patients with some kinds of non-VF cardiac arrest, such as asystole and pulseless electrical activity (PEA). CPR is a combination of techniques that include chest compressions to force blood circulation, and rescue breathing to force respiration.

Properly administered CPR provides oxygenated blood to critical organs of a person in cardiac arrest, thereby minimizing the deterioration that would otherwise occur. As such, CPR can be beneficial for persons experiencing VF, because it slows the deterioration that would otherwise occur while a defibrillator is being retrieved. Indeed, for patients with an extended down-time, survival rates are higher if CPR is administered prior to defibrillation.

Advanced medical devices can actually coach a rescuer who performs CPR. For example, a medical device can issue instructions, and even prompts, for the rescuer to perform CPR more effectively.

Embodiments of the invention address limitations of conventional post-shock treatment of patients.

BRIEF SUMMARY

Embodiments of the disclosed technology are generally directed but not limited to systems and methods for improving survival from sudden cardiac arrest for patients by providing selective post-shock pacing. For patients that are receptive to pacing, external pacing is likely to move more blood than CPR, which may improve patient outcomes. For patients that are not receptive, pacing generally does no good and, thus, CPR is probably better. Electrical capture may be achieved, but no blood flow is produced. In addition, pacing may be pro-arrhythmic. The disclosed technology includes methods of and techniques for distinguishing patients who would be receptive to post-shock pacing from those who would not be receptive to such pacing.

The disclosed methods and techniques for distinguishing patients who would be receptive to post-shock packing from those who would not may include a VF quality analysis, for example. Prior attempts in the field have not included post-shock pacing and have not tied the application of post-shock pacing to VF quality analysis.

BRIEF DESCRIPTION OF THE DRAWINGS

FIG. 1 is a diagram of a scene where an external defibrillator is used to save the life of a person according to embodiments.

FIG. 2 is a table listing two main types of the external defibrillator shown in FIG. 1, and who they might be used by.

FIG. 4 is a flowchart for illustrating a conventional example of a method according to American Heart Association (AHA) guidelines.

DETAILED DESCRIPTION

Figure 3:
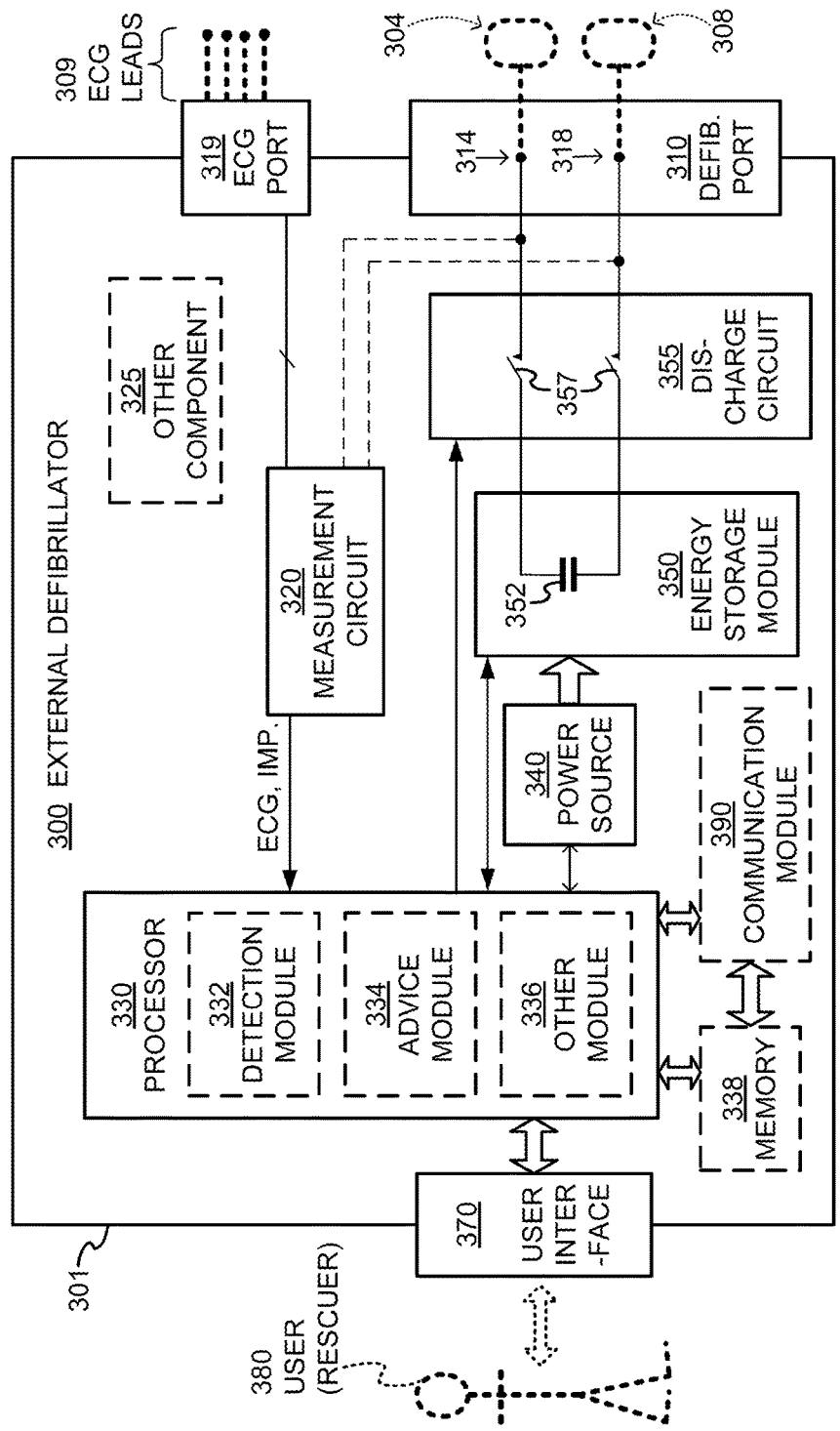
FIG. 3 is a functional block diagram showing components of an external defibrillator, such as the one shown in FIG. 1, which is made according to embodiments.

External pacing, also known as transcutaneous pacing, involves the delivery of multiple electric shocks to a patient in order to pace the patient's heart. Pre-hospital cardiac arrest patients experiencing asystole or bradycardia, however, are not typically receptive to external pacing. Such pacing may produce electrical capture but fail to move blood due to the profound cardiac injury from an extended period of ischemia.

While the American Heart Association (AHA) guidelines call for rescuers to "immediately resume CPR" after a shock, there is evidence that post-shock CPR may not be the best approach for certain people. Indeed, some patients may be receptive to external pacing and, for such patients, pacing may be a more effective therapy for them than CPR.

The inventors identified beneficial methods and systems of determining whether to provide post-shock pacing to patients, and, if determined to be beneficial, then selectively providing the post-shock pacing to certain patients but not to others.

FIG. 1 is a diagram of a defibrillation scene. A person 82 is lying on their back. Person 82 could be a patient in a hospital, or someone found unconscious, and then turned to be on their back. Person 82 is experiencing a condition in their heart 85, which could be Ventricular Fibrillation (VF).

A portable external defibrillator 100 has been brought close to person 82. At least two defibrillation electrodes 104, 108 are usually provided with external defibrillator 100, and are sometimes called electrodes 104, 108. Electrodes 104, 108 are coupled with external defibrillator 100 via respective electrode leads 105, 109. A rescuer (not shown) has attached electrodes 104, 108 to the skin of person 82. Defibrillator 100 is administering, via electrodes 104, 108, a brief, strong electric pulse 111 through the body of person 82. Pulse 111, also known as a defibrillation shock, goes also through heart 85, in an attempt to restart it, for saving the life of person 82.

Defibrillator 100 can be one of different types, each with different sets of features and capabilities. The set of capabilities of defibrillator 100 is determined by planning who would use it, and what training they would be likely to have. Examples are now described.

FIG. 2 is a table listing two main types of external defibrillators, and who they are primarily intended to be used by. A first type of defibrillator 100 is generally called a defibrillator-monitor, because it is typically formed as a single unit in combination with a patient monitor. A defibrillator-monitor is sometimes called monitor-defibrillator. A defibrillator-monitor is intended to be used by persons in the medical professions, such as doctors, nurses, paramedics, emergency medical technicians, etc. Such a defibrillator-monitor is intended to be used in a pre-hospital or hospital scenario.

As a defibrillator, the device can be one of different varieties, or even versatile enough to be able to switch among different modes that individually correspond to the varieties. One variety is that of an automated defibrillator, which can determine whether a shock is needed and, if so, charge to a predetermined energy level and instruct the user to administer the shock. Another variety is that of a manual defibrillator, where the user determines the need and controls administering the shock.

As a patient monitor, the device has features additional to what is minimally needed for mere operation as a defibrillator. These features can be for monitoring physiological indicators of a person in an emergency scenario. These physiological indicators are typically monitored as signals. For example, these signals can include a person's full ECG (electrocardiogram) signals, or impedance between two electrodes. Additionally, these signals can be about the person's temperature, non-invasive blood pressure (NIBP), arterial oxygen saturation/pulse oximetry (SpO2), the concentration or partial pressure of carbon dioxide in the respiratory gases, which is also known as capnography, and so on. These signals can be further stored and/or transmitted as patient data.

A second type of external defibrillator 100 is generally called an AED, which stands for "Automated External Defibrillator". An AED typically makes the shock/no shock determination by itself, automatically. Indeed, it can sense enough physiological conditions of the person 82 via only the shown defibrillation electrodes 104, 108 of FIG. 1. In its present embodiments, an AED can either administer the shock automatically, or instruct the user to do so, e.g. by pushing a button. Being of a much simpler construction, an AED typically costs much less than a defibrillator-monitor. As such, it makes sense for a hospital, for example, to deploy AEDs at its various floors, in case the more expensive defibrillator-monitor is more critically being deployed at an Intensive Care Unit, and so on.

AEDs, however, can also be used by people who are not in the medical profession. More particularly, an AED can be used by many professional first responders, such as policemen, firemen, etc. Even a person with only first-aid training can use one. And AEDs increasingly can supply instructions to whoever is using them.

AEDs are thus particularly useful, because it is so critical to respond quickly, when a person suffers from VF. Indeed, the people who will first reach the VF sufferer may not be in the medical professions.

Increasing awareness has resulted in AEDs being deployed in public or semi-public spaces, so that even a member of the public can use one, if they have obtained first aid and CPR/AED training on their own initiative. This way, defibrillation can be administered soon enough after the onset of VF, to hopefully be effective in rescuing the person.

There are additional types of external defibrillators, which are not listed in FIG. 2. For example, a hybrid defibrillator can have aspects of an AED, and also of a defibrillator-monitor. A usual such aspect is additional ECG monitoring capability.

FIG. 3 is a diagram showing components of an external defibrillator 300 made according to embodiments. These components can be, for example, in external defibrillator 100 of FIG. 1. Plus, these components of FIG. 3 can be provided in a housing 301, which is also known as casing 301.

External defibrillator 300 is intended for use by a user 380, who would be the rescuer. Defibrillator 300 typically includes a defibrillation port 310, such as a socket in housing 301. Defibrillation port 310 includes nodes 314, 318. Defibrillation electrodes 304, 308, which can be similar to electrodes 104, 108, can be plugged in defibrillation port 310, so as to make electrical contact with nodes 314, 318, respectively. It is also possible that electrodes can be connected continuously to defibrillation port 310, etc. Either way, defibrillation port 310 can be used for guiding via electrodes to person 82 an electrical charge that has been stored in defibrillator 300, as will be seen later in this document.

If defibrillator 300 is actually a defibrillator-monitor, as was described with reference to FIG. 2, then it will typically also have an ECG port 319 in housing 301, for plugging in ECG leads 309. ECG leads 309 can help sense an ECG signal, e.g. a 12-lead signal, or from a different number of leads. Moreover, a defibrillator-monitor could have additional ports (not shown), and a software upgrade module 325 configured to cause a software application pertaining to the defibrillator 300 to be upgraded responsive to certain conditions and/or events.

Defibrillator 300 also includes a measurement circuit 320. Measurement circuit 320 receives physiological signals from ECG port 319, and also from other ports, if provided. These physiological signals are sensed, and information about them is rendered by circuit 320 as data, or other signals, etc.

If defibrillator 300 is actually an AED, it may lack ECG port 319. Measurement circuit 320 can obtain physiological signals through nodes 314, 318 instead, when defibrillation electrodes 304, 308 are attached to person 82. In these cases, a person's ECG signal can be sensed as a voltage difference between electrodes 304, 308. Plus, impedance between electrodes 304, 308 can be sensed for detecting, among other things, whether these electrodes 304, 308 have been inadvertently disconnected from the person.

Defibrillator 300 also includes a processor 330. Processor 330 may be implemented in any number of ways. Such ways include, by way of example and not of limitation, digital and/or analog processors such as microprocessors and digital-signal processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 330 can be considered to have a number of modules. One such module can be a detection module 332, which senses outputs of measurement circuit 320. Detection module 332 can include a VF detector. Thus, the person's sensed ECG can be used to determine whether the person is experiencing VF.

Another such module in processor 330 can be an advice module 334, which arrives at advice based on outputs of detection module 332. Advice module 334 can include a Shock Advisory Algorithm, implement decision rules, and so on. The advice can be to shock, to not shock, to administer other forms of therapy, and so on. If the advice is to shock, some external defibrillator embodiments merely report that to the user, and prompt them to do it. Other embodiments further execute the advice, by administering the shock. If the advice is to administer CPR, defibrillator 300 may further issue prompts for it, and so on.

Processor 330 can include additional modules, such as module 336, for other functions. In addition, if other component 325 is indeed provided, it may be operated in part by processor 330, etc.

Defibrillator 300 optionally further includes a memory 338, which can work together with processor 330. Memory 338 may be implemented in any number of ways. Such ways include, by way of example and not of limitation, nonvolatile memories (NVM), read-only memories (ROM), random access memories (RAM), any combination of these, and so on. Memory 338, if provided, can include programs for processor 330, and so on. The programs can be operational for the inherent needs of processor 330, and can also include protocols and ways that decisions can be made by advice module 334. In addition, memory 338 can store prompts for user 380, etc. Moreover, memory 338 can store patient data.

Defibrillator 300 may also include a power source 340. To enable portability of defibrillator 300, power source 340 typically includes a battery. Such a battery is typically implemented as a battery pack, which can be rechargeable or not. Sometimes, a combination is used, of rechargeable and non-rechargeable battery packs. Other embodiments of power source 340 can include AC power override, for where AC power will be available, and so on. In some embodiments, power source 340 is controlled by processor 330.

Defibrillator 300 additionally includes an energy storage module 350. Module 350 is where some electrical energy is stored, when preparing it for sudden discharge to administer a shock. Module 350 can be charged from power source 340 to the right amount of energy, as controlled by processor 330. In typical implementations, module 350 includes one or more capacitors 352, and so on.

Defibrillator 300 moreover includes a discharge circuit 355. Circuit 355 can be controlled to permit the energy stored in module 350 to be discharged to nodes 314, 318, and thus also to defibrillation electrodes 304, 308. Circuit 355 can include one or more switches 357. Those can be made in a number of ways, such as by an H-bridge, and so on.

Defibrillator 300 further includes a user interface 370 for user 380. User interface 370 can be made in any number of ways. For example, interface 370 may include a screen, to display what is detected and measured, provide visual feedback to the rescuer for their resuscitation attempts, and so on. Interface 370 may also include a speaker, to issue voice prompts, etc. Interface 370 may additionally include various controls, such as pushbuttons, keyboards, and so on. In addition, discharge circuit 355 can be controlled by processor 330, or directly by user 380 via user interface 370, and so on.

Defibrillator 300 can optionally include other components. For example, a communication module 390 may be provided for communicating with other machines. Such communication can be performed wirelessly, or via wire, or by infrared communication, and so on. This way, data can be communicated, such as patient data, incident information, therapy attempted, CPR performance, and so on.

A feature of a defibrillator can be CPR-prompting. Prompts are issued to the user, visual or by sound, so that the user can administer CPR. Examples are taught in U.S. Pat. Nos. 6,334,070 and 6,356,785. As described in further detail below, embodiments of defibrillator 300 include other components 325 and/or modules 336 to determine when to provide post-shock CPR pauses and/or pacing to certain patients but not to others.

As used herein, the term rescuer generally refers to a medical professional or other user or operator of a medical device, such as a defibrillator, monitor, and/or chest compressor, in connection with coming to the aid of a person experiencing a medical emergency. For example, such person—generally referred to herein as a patient—may have become unresponsive.

FIG. 4 is a flowchart for illustrating a conventional example of a method 400 according to American Heart Association (AHA) guidelines, which include a number changes to the resuscitation protocol in order to place renewed emphasis on delivery of chest compressions to circulate blood during cardiac arrest. One of these changes is, after delivery of a defibrillation shock to a patient, for the rescuer to begin (or resume) chest compressions very quickly after delivery of a shock, without pausing to analyze the heart rhythm or check for a pulse or other signs of circulation.

It should be noted that approaches associated with immediately resuming chest compressions after delivery of a shock may unfortunately cause certain patients to experience refibrillation. Such refibrillation could happen after every shock, consequently trapping the patient in VF.

At 402, a determination is made that the patient is non-responsive, e.g., he or she is not breathing at all or can accomplish no more than occasional gasps for air. At 404, a rescuer is instructed, e.g., by a defibrillator, to begin performing CPR on the patient. At 406, a defibrillator assesses the patient's heart rhythm.

Responsive to a determination that the patient is deemed shockable (see 408), e.g., there is VF or pulseless VT, the defibrillator instructs the rescuer to deliver a single shock to the patient, e.g., using the defibrillator, and then immediately resume CPR, as indicated at 410 and 412, respectively.

Responsive to a determination that the patient is deemed not shockable (see 414), e.g., there is PEA or asystole, the defibrillator does not provide any instruction with regard to delivering a shock to the patient but does instruct the rescuer to immediately resume CPR, as indicated at 416.

At 418, the rescuer may be prompted, e.g., by the defibrillator, to perform advanced life support techniques, including but not limited to considering an advanced airway, performing continuous chest compressions after the advanced airway is in place, consider capnography, obtain IV/IO access, consider vasopressors and antiarrhythmics, and correct reversible causes.

At 420, the rescuer may be prompted, e.g., by the defibrillator, to perform immediate post-cardiac arrest monitoring and support techniques, including but not limited to a 12-lead ECG, perfusion (or reperfusion), oxygenation and ventilation, temperature control, and reversible causes.

It has been long suspected that the performing of chest compressions on a patient can result in refibrillation of the patient's heart. Indeed, research indicates that refibrillation often occurs within the first few compressions when compressions are restarted after defibrillation, regardless of whether the pause in performing compressions after the shock was short or prolonged.

Some patients are prone to experiencing such refibrillation. Patients that are particularly prone to refibrillation are not necessarily people that have poor prospects of long-term survival. So, any approach that improves care for such patients will generally impact outcomes in a positive manner.

Figure 5:
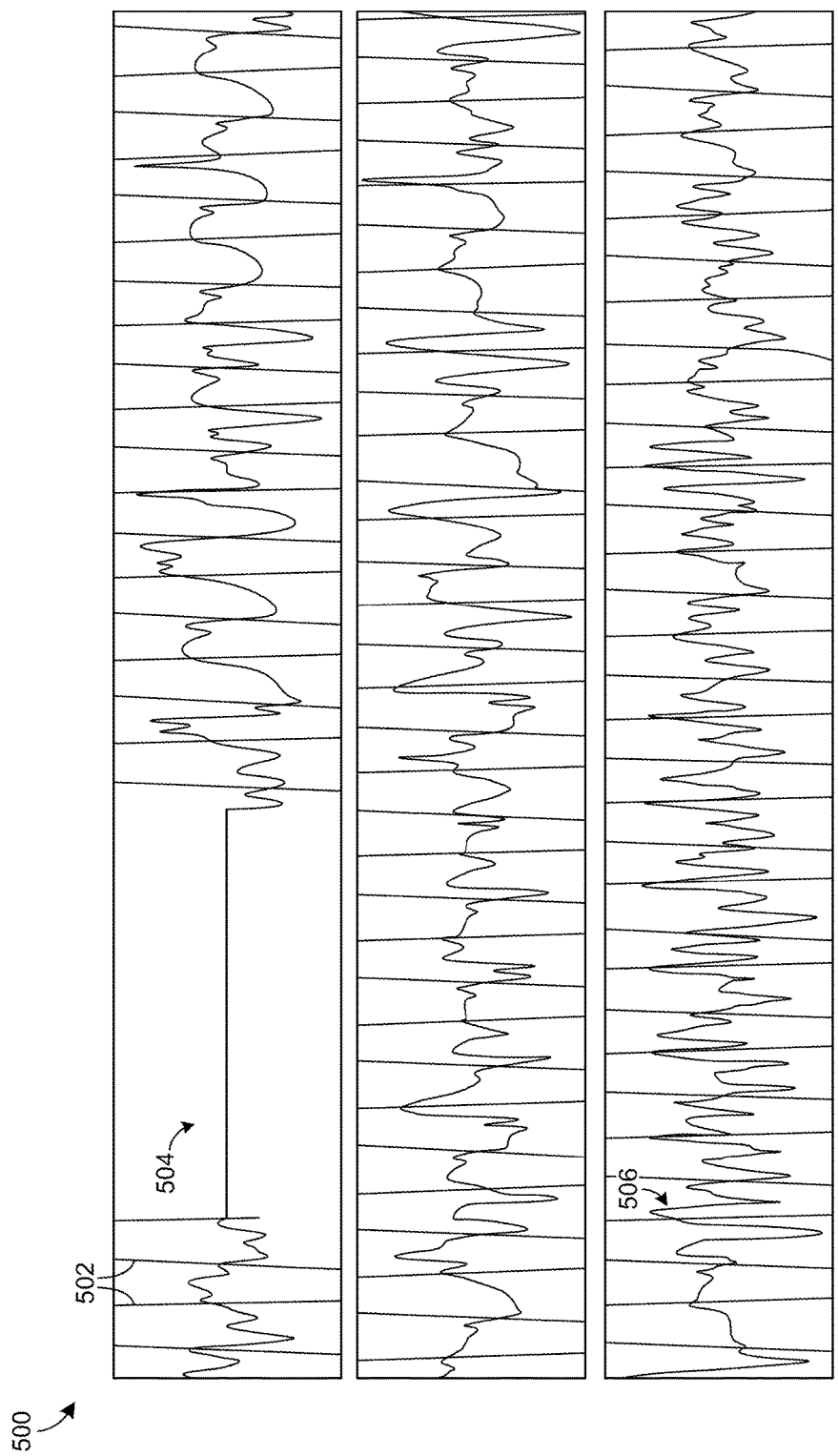
FIGS. 5 and 6 are time diagrams of patient ECG data in the form of signals in a situation where a mechanical device is used to provide nearly continuous chest compressions to the patient.
Figure 6:
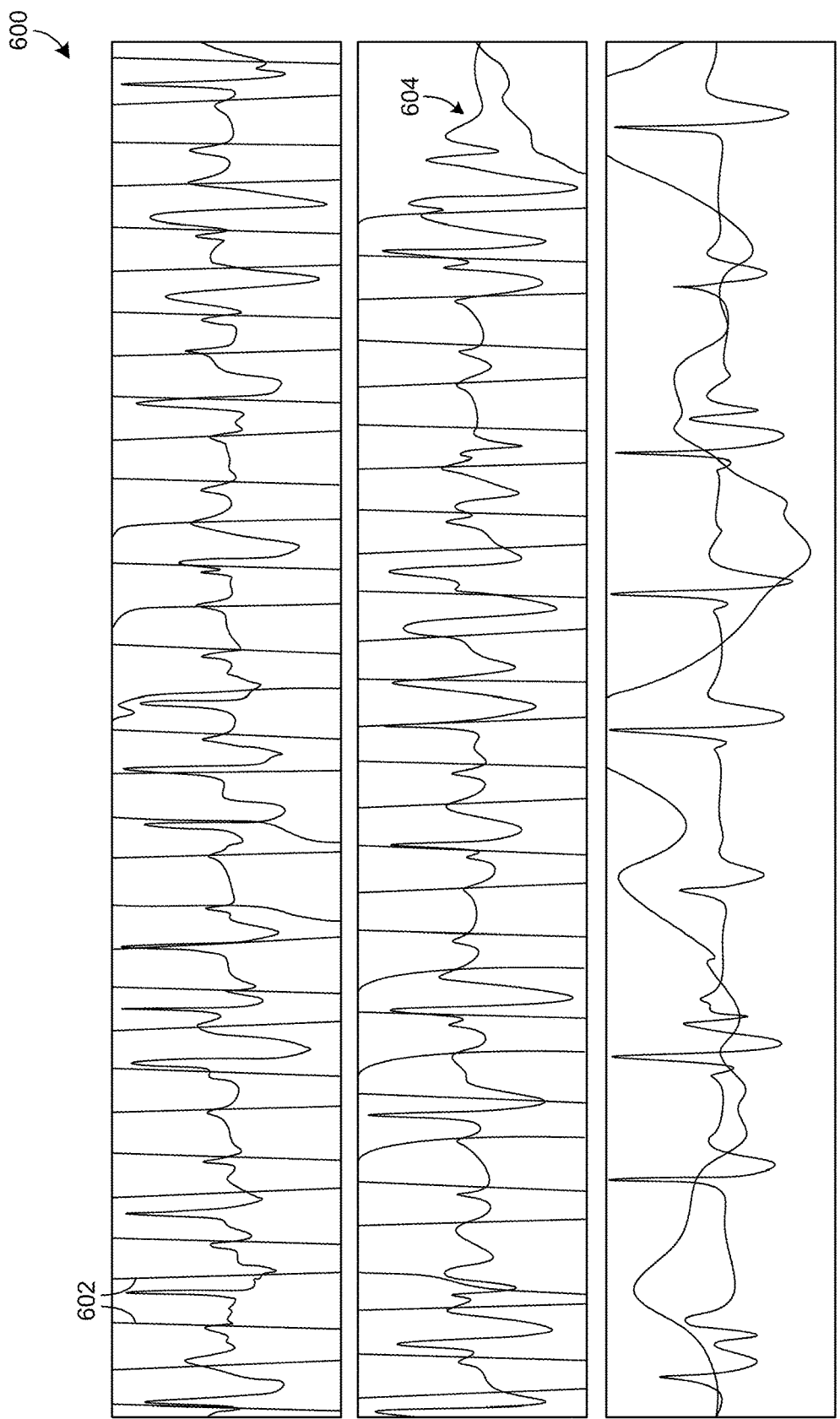

FIGS. 5 and 6 are time diagrams 500 and 600, respectively, of patient ECG data in the form of signals in a situation where a mechanical device is used to provide nearly continuous chest compressions (e.g., 502) to the patient. In the example, VF is repeatedly terminated by a defibrillation shock (see 504) but recurs five times within 10-20 seconds under ongoing chest compressions. Only the first recurrence, which starts at 506, is visible in the figure.

In the example, the shock (at 504) terminates VF, and ventricular complexes can be seen on the compression corrupted ECG for the next 18 seconds or so; the heart goes back into fibrillation (at 506) at that point, and the fibrillation continues until it is recognized at the next pause in compressions, which occurs almost two full minutes later.

In the time diagram 600 illustrated by FIG. 6, one can see that the patient stayed out of VF the sixth time for more than a minute of chest compressions (e.g., 602) and, after the chest compression device was turned off (e.g., once the chest compressions stopped at 602), the patient's heart resumed spontaneous circulation, as can be seen starting at 604.

From the appearance of the ECG shortly after each of the earlier shocks, one can gauge that return of spontaneous circulation (ROSC) could have occurred earlier if the chest compressions had been paused for a while after the shocks. In the example, the sixth shock was a full 18 minutes after the first shock and, arguably, the patient would have been better off if spontaneous circulation could have returned sooner. That is, the patient likely would have had less low-flow time and, consequently, would have experienced less ischemia injury.

In certain embodiments, the rescuer may be instructed to pause after each shock. In alternative embodiments, the rescuer may be instructed to pause after certain shocks. In such embodiments, protocols may be adjusted so that, after every nth shock (e.g., every other shock or every third shock), the rescuer may be instructed to refrain from administering chest compressions for a period of time and, instead, check for a pulse. Instructions for these approaches may be built into the voice prompts of defibrillator devices and/or stand-alone CPR coaching devices, for example, TrueCPR™ available from Physio-Control, Inc., of Redmond, Wash.

In certain embodiments, the rescuer may be instructed to pause under certain conditions. The device is able to quickly check the ECG to determine whether an organized rhythm with narrow complexes and some minimal rate was present and, if not, prompt for immediate resumption of chest compressions. Without a narrow-complex, organized rhythm of at least 40 beats per minute, there almost certainly will be no pulse.

In certain embodiments, the rescuer may be instructed to pause after delivery of a shock only when the pre-shock VF was of a certain (e.g., good) quality. If the VF analyzed before the shock was of a different (e.g., "not good" or coarse) quality, there is likely to be a pulse after the shock. So, a "shock predictive" algorithm may be used to assess the VF; the resulting "viability index" may be used to select prompting for a post-shock pause (e.g., in the case of very coarse VF) or no post-shock pause (e.g., for all others).

In certain embodiments, airway $CO_2$ measurements taken before a shock may be used to determine whether the rescuer should implement a post-shock pause. If the airway $CO_2$ is not getting up to a certain threshold, e.g., 15 mmHg, during chest compressions before the shock, there almost certainly will be no pulse after the shock. The airway $CO_2$ measurements may be used in this manner to select prompting for the rescuer to implement a post-shock pause or no post-shock pause.

Alternatively or in addition thereto, airway $CO_2$ measurements taken during a post-shock pause may be used to determine quickly whether there is circulation in the patient. The rescuer may take advantage of a post-shock pause to administer at least two breaths. If the airway end-tidal $CO_2$ (ETCO2) for the expiration of the first breath is above a certain threshold, e.g., 15 mmHg, and the airway ETCO2 for the expiration of the next breath is at least a certain amount higher, e.g., 5 mmHg, the rescuer may be prompted to perform an immediate pulse check; otherwise, the rescuer may be prompted to start performing chest compressions.

Figure 7:
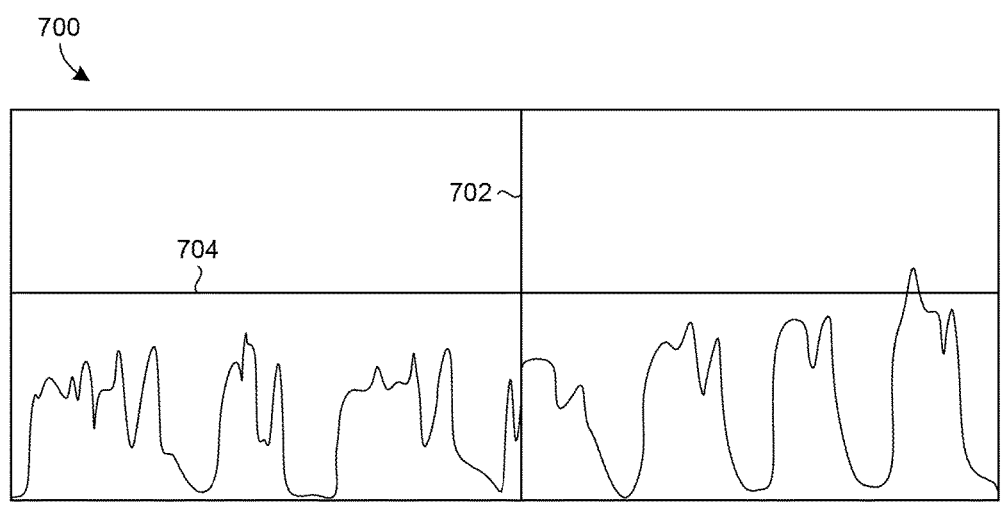
FIG. 7 is a time diagram of patient $CO_2$ data in the form of signals in a situation where a chest compression device has provided compressions to the patient until a certain time, at which point the chest compression device was turned off.

FIG. 7 is a time diagram 700 of patient $CO_2$ data in the form of signals in a situation where a chest compression device, for example the LUCAS® Chest Compression System available from Physio-Control, Inc., of Redmond, Wash., has provided compressions to the patient until a certain time (indicated by 702), at which point the chest compression device was turned off. In the time diagram 700, each horizontal square represents 0.8 seconds and each vertical square represents approximately 6 mmHg. The time diagram 700 illustrates how the patient's ETCO2 increased progressively with each breath after the chest compression device had been turned off, eventually exceeding a certain threshold 704, e.g., 15 mmHg Indeed, in the example, the patient's ETCO2 continued to progressively increase for many breaths after those represented in the time diagram 700.

In certain embodiments, Doppler ultrasound taken during a post-shock pause may be used to determine quickly whether there is circulation in the patient. The audio signal provided by Doppler systems may enable the human ear to quickly recognize return of circulation, but the probe should be rapidly and reliably positioned so that the patient's circulation may be reliably detected, which can be a challenge.

In connection with various embodiments described herein, the capability to sense relevant information and diagnosis may be combined with the capability to inform or automatically guide a user, e.g., rescuer, through a certain sequence of activities. Such combination may be implemented in connection with or by any of a number of devices such as a defibrillator, an AED, or a monitor. For example, some defibrillators such as the LIFEPAK® 15 available from Physio-Control, Inc., of Redmond, Wash. can make $CO_2$ measurements through an integrated ETCO2 monitor. For example, a monitor having airway $CO_2$ sensing capability typically has integrated therein algorithms operable to assist the rescuer in rapidly detecting ROSC during a post-shock pause. Such $CO_2$ measurement capability can be used as described above to facilitate determination of whether a rescuer should implement post-shock pacing.

In situations where the defibrillator or monitor removes any compression artifact from the ECG sufficiently to be able to accurately evaluate the patient's heart rhythm during chest compressions, and reliably sense through the compressions that a shock successfully terminated VF but that VF then recurred in less than 20 seconds, such device may advantageously provide that information to the operator and/or provide voice prompts guiding the rescuer to pause compressions at the time of—and just after—the next defibrillation shock.

Mechanical chest compression systems are generally effective at providing continuous and consistent automated compressions and, therefore, may be particularly "good" at trapping patients in a repeating defibrillate/refibrillate cycle. Consequently, it would be beneficial to have specific logic built into such devices to provide a graceful exit from such a cycle. In certain embodiments, the compression device may instruct the user to turn the device off for at least some, and perhaps all defibrillation attempts, e.g., after every second, third, or nth shock.

In certain embodiments, a chest compression device may be in communication with a defibrillator so that the defibrillation shocks are positively identified, e.g., via notification or confirmation from the defibrillator. Alternatively, if the chest compression device is able to sense an abrupt change in chest stiffness, e.g., using its force and displacement sensors, the device may be able to identify the moment of defibrillation shock delivery.

The current medical consensus is that external pacing in pre-hospital cardiac arrest patients is beneficial in few, if any, circumstances, while chest compressions have been proven to be critical to survival. There is evidence, however, that there may be some pre-hospital cardiac arrest patients for whom post-shock pacing may be effective and, possibly, preferable to chest compressions.

Figure 8:
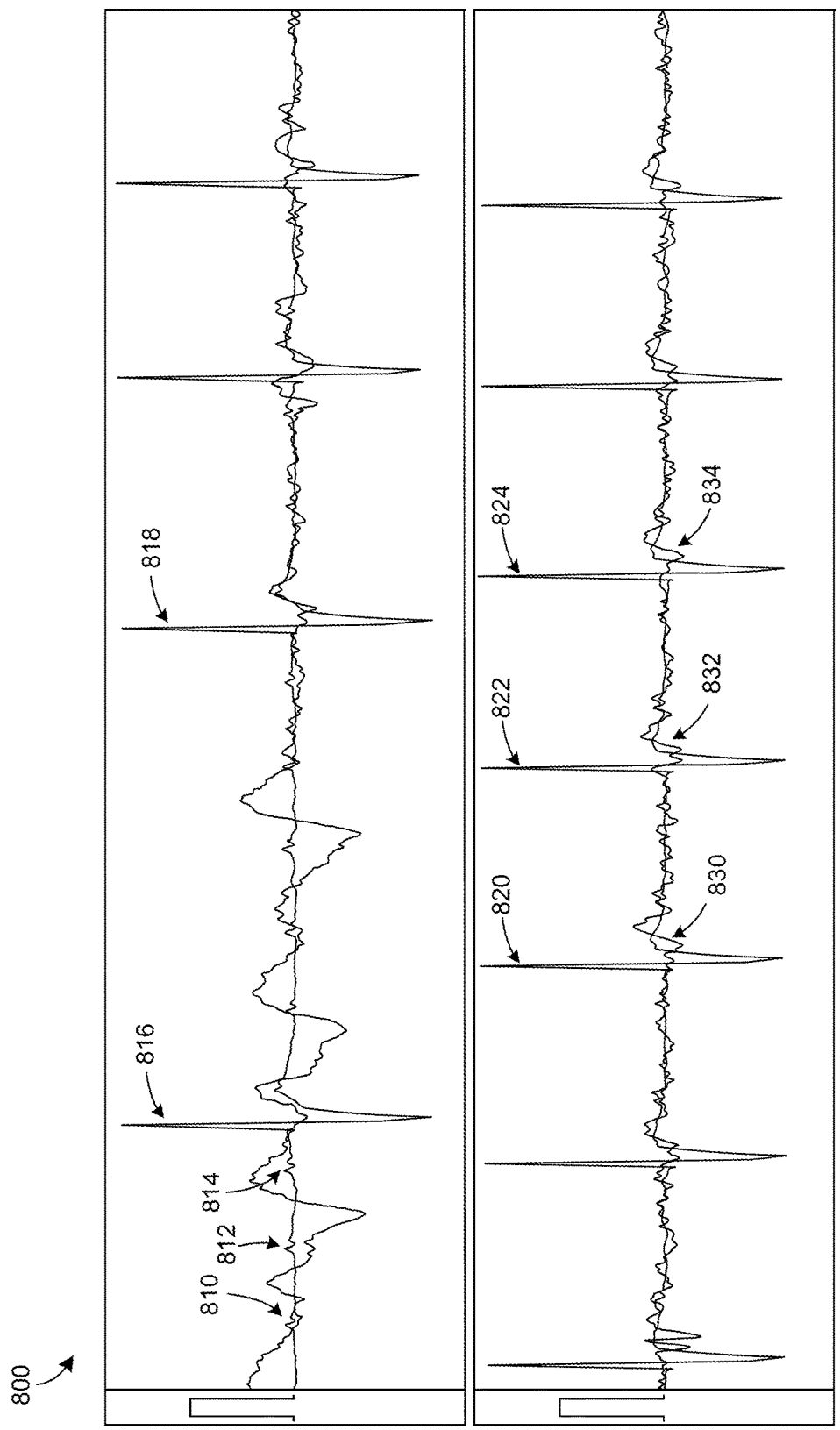
FIG. 8 is a time diagram of patient ECG data in the form of signals in a situation where a pre-hospital cardiac arrest patient was treated with a defibrillator, such as an AED.

FIG. 8 is a time diagram 800 of patient ECG data in the form of signals in a situation where a pre-hospital cardiac arrest patient was treated with a defibrillator, such as an AED. In the example, the patient has extreme bradycardia: while p-waves (e.g., 810, 812, 814) can be seen, they are only intermittently associated with QRS complexes (e.g., 816, 818), thus resulting in a low heart rate that is insufficient to support perfusion.

When certain QRS complexes (e.g., 820, 822, 824) do occur, however, the impedance channel shows impedance artifacts (e.g., 830, 832, 834) that are indicative of blood flow. That is, the patient's heart can move blood when it beats, but it doesn't beat very fast. It is likely that the reason this patient is experiencing bradycardia is some sort of heart block. This patient is thus an ideal candidate for external pacing because it appears that, if the ventricles are triggered, they will move blood.

It should be noted that the patient in the example is not a typical pre-hospital cardiac arrest patient because, whereas post-shock asystole and/or bradycardia are common, observable p-waves have not been previously documented, and neither has evidence of perfusion in a pre-hospital patient experiencing bradycardia.

The functions of this description may be implemented by one or more devices that include logic circuitry. The device performs functions and/or methods as are described in this document. The logic circuitry may include a processor that may be programmable for a general purpose, or dedicated, such as microcontroller, a microprocessor, a Digital Signal Processor (DSP), etc. For example, the device may be a digital computer like device, such as a general-purpose computer selectively activated or reconfigured by a computer program stored in the computer. Alternately, the device may be implemented by an Application Specific Integrated Circuit (ASIC), etc.

Moreover, methods are described below. The methods and algorithms presented herein are not necessarily inherently associated with any particular computer or other apparatus. Rather, various general-purpose machines may be used with programs in accordance with the teachings herein, or it may prove more convenient to construct more specialized apparatus to perform the required method steps. The required structure for a variety of these machines will become apparent from this description.

In all cases there should be borne in mind the distinction between methods in this description, and the method of operating a computing machine. This description relates both to methods in general, and also to steps for operating a computer and for processing electrical or other physical signals to generate other desired physical signals.

Programs are additionally included in this description, as are methods of operation of the programs. A program is generally defined as a group of steps leading to a desired result, due to their nature and their sequence. A program is usually advantageously implemented as a program for a computing machine, such as a general-purpose computer, a special purpose computer, a microprocessor, etc.

Storage media are additionally included in this description. Such media, individually or in combination with others, have stored thereon instructions of a program made according to the invention. A storage medium according to the invention is a computer-readable medium, such as a memory, and is read by the computing machine mentioned above.

Performing the steps or instructions of a program requires physical manipulations of physical quantities. Usually, though not necessarily, these quantities may be transferred, combined, compared, and otherwise manipulated or processed according to the instructions, and they may also be stored in a computer-readable medium. These quantities include, for example electrical, magnetic, and electromagnetic signals, and also states of matter that can be queried by such signals. It is convenient at times, principally for reasons of common usage, to refer to these quantities as bits, data bits, samples, values, symbols, characters, images, terms, numbers, or the like. It should be borne in mind, however, that all of these and similar terms are associated with the appropriate physical quantities, and that these terms are merely convenient labels applied to these physical quantities, individually or in groups.

This detailed description is presented largely in terms of flowcharts, display images, algorithms, and symbolic representations of operations of data bits within at least one computer readable medium, such as a memory. Indeed, such descriptions and representations are the type of convenient labels used by those skilled in programming and/or the data processing arts to effectively convey the substance of their work to others skilled in the art. A person skilled in the art of programming may use these descriptions to readily generate specific instructions for implementing a program according to the present invention.

Often, for the sake of convenience only, it is preferred to implement and describe a program as various interconnected distinct software modules or features, individually and collectively also known as software. This is not necessary, however, and there may be cases where modules are equivalently aggregated into a single program with unclear boundaries. In any event, the software modules or features of this description may be implemented by themselves, or in combination with others. Even though it is said that the program may be stored in a computer-readable medium, it should be clear to a person skilled in the art that it need not be a single memory, or even a single machine. Various portions, modules or features of it may reside in separate memories, or even separate machines. The separate machines may be connected directly, or through a network, such as a local access network (LAN), or a global network, such as the Internet.

It will be appreciated that some of these methods may include software steps that may be performed by different modules of an overall software architecture. For example, data forwarding in a router may be performed in a data plane, which consults a local routing table. Collection of performance data may also be performed in a data plane. The performance data may be processed in a control plane, which accordingly may update the local routing table, in addition to neighboring ones. A person skilled in the art will discern which step is best performed in which plane.

An economy is achieved in the present document in that a single set of flowcharts is used to describe both programs, and also methods. So, while flowcharts are described in terms of boxes, they can mean both method and programs.

For this description, the methods may be implemented by machine operations. In other words, embodiments of programs are made such that they perform methods of the invention that are described in this document. These may be optionally performed in conjunction with one or more human operators performing some, but not all of them. As per the above, the users need not be collocated with each other, but each only with a machine that houses a portion of the program. Alternately, some of these machines may operate automatically, without users and/or independently from each other.

Methods are now described.

Figure 9:
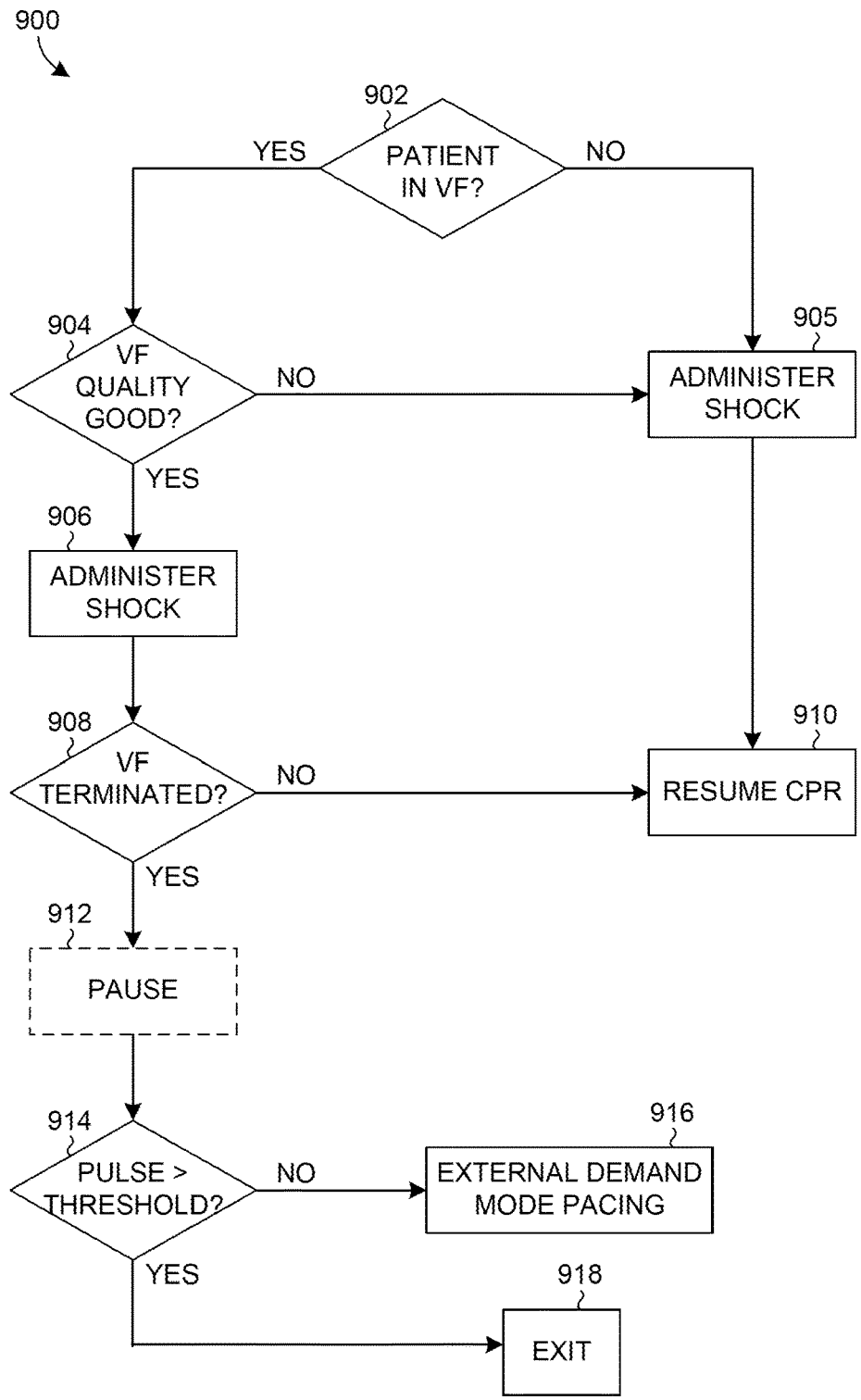
FIG. 9 is a flowchart for illustrating methods according to embodiments of the disclosed technology.

FIG. 9 shows a flowchart 900 for describing methods according to embodiments of the disclosed technology. According to an initial operation 902, a determination is made as to whether the patient is currently experiencing VF (or VT). An AED could do this with an automatic algorithm, for example. A user of a manual defibrillator could do this by looking at the screen.

Responsive to a determination that the patient is indeed experiencing VF, a subsequent determination is made as to the quality of the VF, as indicated by an operation at 904. Any of a number of various measures of VF quality may be used, including but not limited to amplitude spectral area (AMSA) and median slope, for example. In alternative embodiments, the VF Quality analysis may be replaced by any suitable patient signal analysis such as those described herein, including but not limited to analysis based on patient ETCO2 values.

Responsive to a determination that the VF quality is "not good," the rescuer is instructed to administer an electric shock to the patient and then resume CPR (e.g., immediate chest compressions), as indicated by operations at 905 and 910, respectively; otherwise, the rescuer is instructed, e.g., by a defibrillator, to administer an electric shock to the patient, e.g., using the same defibrillator, as indicated by an operation at 906, and then a subsequent determination is made as to whether the VF has terminated, as indicated by an operation at 908.

Responsive to a determination that VF has not terminated, the rescuer is instructed to resume CPR, as indicated by the operation at 910; otherwise, a determination is made as to whether the patient has a pulse that exceeds a particular threshold, as indicated by an operation at 914. In certain embodiments, for example, the threshold may be selected based on the normal bradycardia threshold, e.g., 60-80 beats per minute. In other embodiments, the threshold may be zero (i.e., when no pulse can be detected) An optional operation at 912 may instruct the rescuer to pause, e.g., for 15-20 seconds, before checking the patient's pulse, e.g., to allow time for the patient's circulation to develop.

Responsive to a determination that the patient does not exceed the threshold, the rescuer is instructed to begin external demand-mode pacing, as indicated by an operation at 916. Such pacing generally only delivers pulses if the patient's intrinsic rate is slower than a set pacing rate. Should the patient's intrinsic rate accelerate, the pacing would automatically stop. In alternative embodiments, synchronized CPR may be performed with the demand-mode pacing.

Responsive to a determination that the patient does exceed the threshold, processing ends, as indicated at 918, because the patient is in ROSC.

In certain embodiments, an AED may perform the operations of the method 900 automatically, either in sequence or simultaneously, or a combination thereof. In such embodiments, the user may then be prompted to stand clear for the shock and also for the pacing. The pacing current level would typically be set at a relatively high level, e.g., 200 mA, in order to ensure capture. The pacing rate would typically be set at in a normal range, e.g., 80-120 BPM.

In certain embodiments, the AED may be set up to pace for a fixed amount of time, e.g. one minute, or until the patient regains consciousness (e.g., as indicated by a button press by the operator), until the patient refibrillates, or until the patient's intrinsic rate exceeds the pacing rate, for example.

In a manual defibrillator, some of the operations of the illustrated method 900 could be performed manually. For example, if the device determined that the patient had a good VF quality, it is possible for the rescuer to manually activate the post-shock pacing. However, in some embodiments, the defibrillator can be configured so that, in certain situations, it can automatically trigger the pacing to minimize button presses and delays. The rescuer might also want to adjust the pacing current and rate, e.g., in order to optimize hemodynamics. The rescuer can palpate a pulse to verify that pacing has effectively captured the heart. Other patient parameters, such as NIBP, ETCO2, or SpO2 could be used to manually or automatically verify capture and perfusion.

Figure 10:
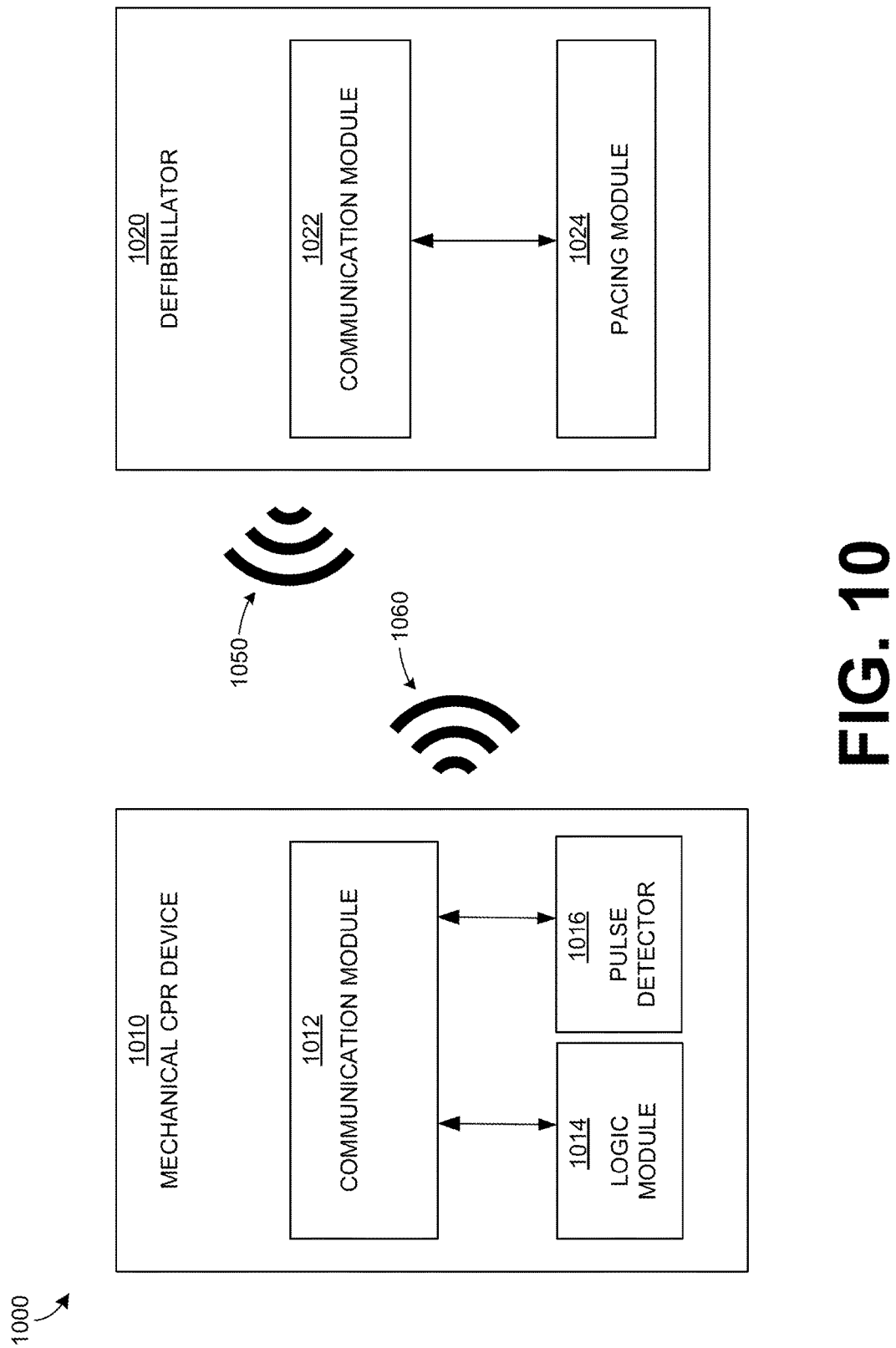
FIG. 10 is a functional block diagram showing a system including a mechanical CPR device, which is made according to embodiments.

FIG. 10 is a functional block diagram showing a system 1000 including a mechanical CPR device 1010, which is made according to embodiments. In the example, the mechanical CPR device 1010 has a communication module 1012 configured to communicate 1050, 1060 with a communication module 1022 of a defibrillator 1020, which may be an external defibrillator or a wearable defibrillator, for example. The communication 1050, 1060 may be via a "hard" connection (e.g., wired) or a wireless connection.

While the example includes a defibrillator 1020, it will be appreciated that, in alternative embodiments, any of a variety of other suitable devices, such as a monitor, may be used to perform the post-shock pacing analysis in place of the defibrillator 1020.

In the example, the defibrillator has a pacing module 1024 configured to control pacing, such as post-shock pacing, delivered to a patient. The mechanical CPR device 1010 has a logic module 1014 configured to control delivery of chest compressions to the patient, for example.

Either or both of the pacing module 1024 and logic module 1014 may perform certain operations responsive to information received, directly or indirectly, from the other, e.g., by way of the communication modules 1012 and 1022 in accordance with certain embodiments described herein. For example, the mechanical CPR device 1010 may automatically perform a pause operation such as the pause operation 912 of FIG. 9.

Alternatively or in addition thereto, the mechanical CPR device 1010 may have a pulse detector 1016, e.g., a Doppler ultrasound component, configured to detect when a shock has been administered to a patient. In such embodiments, the logic module 1014 may direct the mechanical CPR device 1010 to stop compressions, e.g., to allow the pulse detector 1016 to detect whether the patient has a pulse.

Rather than using VF analysis to determine whether post-shock pacing should be performed, other techniques could be implemented. For example, in situations where the down time is known to be short, in some embodiments the rescuer could be instructed to always apply post shock pacing.

In situations where the patient has a 'high' tissue oximetry measurement, e.g., indicating sufficient blood flow for a period of time, the rescuer could be instructed to apply post-shock pacing. This tissue oximetry measurement is typically measured on the thenar eminence.

In situations where the patient has a 'high' cerebral oximetry measurement, e.g., indicating sufficient blood flow for a period of time, in some embodiments the rescuer could be instructed to apply post-shock pacing.

In certain embodiments, ETCO2 values may be used to determine whether to apply post-shock pacing. For example, because patients having high ETCO2 values are known to be more likely to achieve ROSC and are thus more likely to survive (and may also be more receptive to post-shock pacing, the rescuer may be instructed to apply post-shock pacing if the patient has had a consistently high ETCO2 value for a certain period of time, e.g., four minutes.

In certain embodiments, a rescuer may be instructed to always apply post-shock pacing to patients who exhibit pre-shock non-perfusing VT. While VT is not a common rhythm in pre-hospital cardiac arrest, it does happen in certain patients, particularly in patients who re-arrest. VT is a good-quality rhythm that is typically associated with an increased likelihood of ROSC, so patients exhibiting such VT are generally appropriate candidates for post-shock pacing.

In certain embodiments, a rescuer may be instructed to always apply post-shock pacing to patients who previously experienced ROSC, which generally indicates that the patient is in relatively good condition and may be receptive to pacing. In situations where a patient has ROSC but then refibrillates, post-shock pacing could be applied always after the shock.

Certain alternative embodiments may include the detection of cardiac output associated with QRS complexes for patients experiencing extreme bradycardia. The ECG/impedance tracing for such patients generally include QRS complexes that have impedance evidence of cardiac output (perfusion). Such impedance itself suggests that the patient should be receptive to external pacing, independent of the pre-shock rhythm. If this evidence of cardiac output could be identified while the patient was being treated, it could be used as a basis for deciding whether to apply pacing pulses.

In such scenarios, the pacing pulses would generally not be applied post-shock but, rather, at any time the patient has a bradycardic rhythm with evidence of cardiac output. Detection of cardiac output would generally be based on a specific impedance trace deflection in a particular relationship to the QRS complex. Noise reduction techniques, such as signal averaging, may be used to detect the cardiac output amidst the motion artifact that is often present on the impedance signal.

Other alternative embodiment may include, rather than the performing of either external pacing or CPR (but not both), CPR may be performed during pacing. This would advantageously eliminate the need to choose which therapy to apply. Normally, external pacing requires hundreds of volts to deliver 200 mA to a patient with an impedance level up to 1000 ohms. However, post-shock pacing would not require much voltage because the patient impedance is lower. Accordingly, in some embodiments the post-shock pacing voltage is reduced to a level where manual CPR during post-shock pacing is safe. This could be applied to all patients without the VF analysis, but in one embodiments the compressions are synchronized to the pacing pulses.

In this description, numerous details have been set forth in order to provide a thorough understanding. In other instances, well-known features have not been described in detail in order to not obscure unnecessarily the description.

A person skilled in the art will be able to practice the present invention in view of this description, which is to be taken as a whole. The specific embodiments as disclosed and illustrated herein are not to be considered in a limiting sense. Indeed, it should be readily apparent to those skilled in the art that what is described herein may be modified in numerous ways. Such ways can include equivalents to what is described herein. In addition, the invention may be practiced in combination with other systems.

The following claims define certain combinations and subcombinations of elements, features, steps, and/or functions, which are regarded as novel and non-obvious. Additional claims for other combinations and subcombinations may be presented in this or a related document.

What is claimed is:

1. A medical device, comprising:
a housing;
an energy storage module within the housing configured to store an electrical charge;
a defibrillation port configured to guide via electrodes the stored electrical charge to a person; and
a processor configured to, responsive at least in part to a determination that the person is experiencing ventricular fibrillation (VF), perform a patient signal analysis on an electrocardiogram (ECG) signal corresponding to the person and further determine, based at least in part on a result of the patient signal analysis, whether transcutaneous pacing should be performed on the person subsequent to the defibrillation port guiding the stored electrical charge to the person, wherein the processor is further configured to cause the defibrillation port to provide the transcutaneous pacing to the person via the electrodes.

2. The medical device of claim 1, further comprising:
a user interface, wherein the processor is further configured to cause the user interface to issue a prompt to a user of the medical device instructing the user to cause the stored electrical charge to be guided to the person subsequent to the patient signal analysis.

3. The medical device of claim 2, in which
the processor is further configured to, responsive at least in part to the result of the patient signal analysis, cause the user interface to issue a prompt to a user instructing the user to perform cardiopulmonary resuscitation (CPR) on the person subsequent to the defibrillation port guiding the stored electrical charge to the person.

4. The medical device of claim 2, in which
the processor is further configured to, responsive at least in part to the result of the patient signal analysis being, determine whether the VF has terminated subsequent to the defibrillation port guiding the stored electrical charge to the person.

5. The medical device of claim 4, in which
the processor is further configured to, responsive at least in part to a determination that the VF has not terminated, cause the user interface to issue a prompt to a user instructing the user to perform CPR on the person.

6. The medical device of claim 4, in which
the processor is further configured to, responsive at least in part to a determination that the VF has terminated, cause the user interface to issue a prompt to the user instructing the user to determine the person's pulse rate.

7. The medical device of claim 6, in which
the processor is further configured to cause the user interface to issue a prompt to the user instructing the user to pause for a certain period of time before determining the person's pulse rate.

8. The medical device of claim 6, in which
the processor is configured to cause the defibrillation port to provide the transcutaneous pacing to the person via the electrodes responsive to receiving an input from the user indicating that the person's pulse is below a threshold.

9. The medical device of claim 1, in which
the patient signal analysis is based at least in part on amplitude spectral area (AMSA) and slope.

10. A system, comprising:
an external defibrillator that includes:
a housing;
an energy storage module within the housing configured to store an electrical charge;
a defibrillation port configured to guide via electrodes the stored electrical charge to a person; and
a processor configured to, responsive at least in part to a determination that the person is experiencing ventricular fibrillation (VF), perform a patient signal analysis on an electrocardiogram (ECG) signal corresponding to the person and further determine, based on a result of the patient signal analysis, whether transcutaneous pacing should be performed on the person subsequent to the defibrillation port guiding the stored electrical charge to the person, wherein the processor is further configured to cause the defibrillation port to provide the transcutaneous pacing to the person via the electrodes; and
a chest compression device configured to provide chest compressions responsive at least in part to a signal provided by the defibrillator.

11. The system of claim 10, in which
the processor is configured to cause the stored electrical charge to be guided to the person.

12. The system of claim 11, in which
the chest compression device is configured to provide chest compressions to the person responsive at least in part to a signal provided by the defibrillator, in which the signal provided by the defibrillator is based at least in part on the result of the patient signal analysis.

13. The system of claim 11, in which
the processor is further configured to, responsive to the result of the patient signal analysis, determine whether the VF has terminated subsequent to the defibrillation port guiding the stored electrical charge to the person.

14. The system of claim 13, in which
the processor is further configured to, responsive to a determination that the VF has not terminated, cause the chest compression device to provide chest compressions to the person.

15. The system of claim 13, in which
the processor is further configured to, responsive to a determination that the VF has terminated, instruct a rescuer to determine the person's pulse rate.

16. The system of claim 15, in which
the processor is further configured to instruct the rescuer to pause for a certain period of time before determining the person's pulse rate.

17. The system of claim 15, in which
the processor is configured to cause the defibrillation port to provide the transcutaneous pacing to the person via the electrodes responsive to a determination that the person's pulse rate is below a threshold.

18. A method, comprising:
a medical device determining whether a person is experiencing ventricular fibrillation (VF);
responsive to a determination that the person is experiencing VF, the medical device performing a patient signal analysis on an electrocardiogram (ECG) signal corresponding to the person;
the medical device determining, based at least in part on a result of the patient signal analysis, whether transcutaneous pacing should be performed on the person subsequent to delivery of a stored electrical charge to the person; and
the medical device performing the transcutaneous pacing on the person via the electrodes.

19. The method of claim 18, further comprising:
the medical device determining, responsive to the result of the patient signal analysis, whether the VF has terminated subsequent to the defibrillation port guiding the stored electrical charge to the person.

20. The method of claim 19, further comprising:
the medical device determining, responsive to a determination that the VF has terminated, the person's pulse rate.

21. The method of claim 20, in which:
the medical device performs the transcutaneous pacing on the person responsive at least in part to a determination that the person's rate is below a threshold.

22. The method of claim 21, further comprising:
the medical device stopping the transcutaneous pacing responsive to the person having a pulse that exceeds a rate of the transcutaneous pacing.

23. The method of claim 18, in which
the patient signal analysis comprises a determination as to VF quality.

* * * * *